United States Patent [19]

Merger et al.

[11] 4,290,970

[45] Sep. 22, 1981

[54] PROCESS FOR THE MANUFACTURE OF AROMATIC DI- AND/OR POLYISOCYANATES

[75] Inventors: Franz Merger, Frankenthal; Friedrich Towae, Ludwigshafen, both of Fed. Rep. of Germany

[73] Assignee: BASF Aktiengesellschaft, Ludwigshafen, Fed. Rep. of Germany

[21] Appl. No.: 196,814

[22] Filed: Oct. 14, 1980

[30] Foreign Application Priority Data

Oct. 20, 1979 [DE]  Fed. Rep. of Germany ....... 2942503

[51] Int. Cl.³ .................. C07C 118/00; C07C 125/07
[52] U.S. Cl. ............................... 260/453 P; 560/24; 560/25
[58] Field of Search ............... 260/453 P; 560/24, 25

[56] References Cited

U.S. PATENT DOCUMENTS

| | | | |
|---|---|---|---|
| 2,677,698 | 5/1954 | Deutschman et al. | 560/24 |
| 2,806,051 | 9/1957 | Brockway | 560/24 |
| 3,763,217 | 10/1973 | Brill | 560/24 |
| 3,919,279 | 11/1975 | Rosenthal et al. | 260/453 P |
| 4,080,365 | 3/1978 | Hirai et al. | 560/25 |
| 4,081,472 | 3/1978 | Isumura et al. | 260/453 P |
| 4,100,351 | 7/1978 | Romano et al. | 560/24 |
| 4,146,727 | 3/1979 | Shawl et al. | 560/25 |

*Primary Examiner*—Dolph H. Torrence
*Attorney, Agent, or Firm*—David L. Hedden; Joseph D. Michaels

[57] ABSTRACT

This invention pertains to a process for the preparation of an aromatic di- and/or polyisocyanate comprising the steps of A. preparing an aromatic di- and/or polyurethane by
  1. reacting a primary aromatic di- and/or polyamine with an O-alkyl carbamate at temperatures greater than 100° C.;
  2. separating the ammonia and other by-products from the aromatic di- and/or polyurethane;
B. heating and the aromatic di- and/or polyurethane at temperatures of from 175° C. to 600° C.; and
C. isolating the di- and/or polyisocyanate resulting from step B.

14 Claims, No Drawings

PROCESS FOR THE MANUFACTURE OF AROMATIC DI- AND/OR POLYISOCYANATES

BACKGROUND OF THE INVENTION

1. Field of the Invention

This invention pertains to the preparation of aromatic di- and/or polyisocyanates by thermally cleaving polyurethanes which are prepared by reacting aromatic di-and/or polyamines with O-alkyl carbamates, preferably in the presence of an alcohol and urea.

2. Description of the Prior Art

It is known that aromatic di- and/or polyisocyanates can be prepared by reacting aromatic di- and/or polyamines with phosgene to form the corresponding carbamic acid chloride which can be thermally cleaved into the corresponding di- and/or polyisocyanate. There are several problems with this process: the formation of hydrogen chloride, the toxicity of phosgene, the corrosiveness of the reaction mixtures, and the instability of the solvent. The process is expensive and is difficult to undertake safely. Consequently, there is great interest in producing aromatic di- and polyisocyanates without using chlorine and phosgene.

One method of doing this is by the reaction of carbon dioxide and organic nitro compounds in the presence of noble metals as catalysts at increased temperatures and pressures. See British Pat. No. 1,025,436. Other suitable catalysts are complexes or mixtures of hetero-aromatic compounds and at least one noble metal halide. See U.S. Pat No. 3,576,835 (German Published Application No. 1,815,517). Also, compounds having the general formula $PdL(CO)X_2$ in which L stands for a Lewis acid and X represents a halogen atom are suitable catalysts. See U.S. Pat. Nos. 3,654,279 and 3,781,321. The problems with these methods are that the catalysts are costly, the reaction conditions must be carefully monitored, and the yields are unsatisfactory.

In order to eliminate these drawbacks, it has been suggested that polyisocyanates be prepared by converting aromatic amines and/or nitro compounds into urethanes which can then be thermally cleaved into the corresponding polyisocyanates. Many attempts have been made to prepare urethanes which can be converted to polyisocyanates. German Published Application No. 2,160,111 (U.S. Pat. No. 3,763,217) and German Published Application No. 2,716,340 (U.S. Pat No. 4,100,351) describe processes for the manufacture of arylurethanes from arylamines such as toluene diamine and/or N-arylamides and dimethyl carbonate in the presence of a Lewis acid. However, dimethyl carbonate must be produced from phosgene and methanol or, according to more recent suggestions, from carbon monoxide and methanol by means of a technically difficult to implement co-oxidation process. However, the co-oxidation process is expensive when compared to the process using phosgene and there is a rather low rate of reaction. Also, N-alkyl-arylamines are formed during the reaction.

German Published Application No. 1,568,044 (U.S. Pat. No. 3,467,694) describes a process by which urethanes can be produced by reacting organic nitro compounds, carbon monoxide, and hydroxyl-containing compounds in the presence of a catalyst which consists of a noble metal and a Lewis acid under essentially anhydrous conditions. The reaction takes place in the absence of hydrogen at increased pressure and at temperatures above 150° C. German Published Application No. 2,343,826 (U.S. Pat. No. 3,895,054) also describes a process by which urethanes are produced from hydroxyl-group containing compounds, carbon monoxide, and nitro-, nitroso-, azo- and azoxy-group containing compounds in the presence of sulfur, selenium, a sulfur and/or selenium compound, and at least one base and/or water. German Published Application No. 2,623,694 (U.S. Pat. No. 4,080,365) describes the manufacture of aromatic urethanes from the above-referenced raw materials in the presence of selenium-containing catalyst systems as well as specific aromatic amino and urea compounds.

However, these processes have considerable drawbacks. They utilize toxic carbon monoxide as a raw material and catalysts which are toxic, or form toxic compounds during the reaction, such as selenium and hydrogen sulfide, or catalysts which are very expensive and difficult to recycle, such as palladium, and they require high technical expenditures with costly safety measures. In addition to this, they can not be used for the synthesis of polyurethanes of the polymethylene polyphenylene urethane type, the potential precursors of one of the technically most important polyisocyanates, crude MDI.

It is also known that phenyl urethane, which is advantageously accessable and which is produced from nitro benzene, carbon monoxide and alcohol, can, according to German Pat. No. 1,042,891 and German Published Application No. 2,832,379, be processed in two stages by condensation with formaldehyde in the presence of large quantities of a strong acid to form methylene-bis-phenyl urethanes and polymethylene polyphenyl urethane (crude MDU). These products can be thermally cleaved to form crude MDI. However, this process is technically not sufficiently flexible and is complicated. It is not sufficiently flexible because of the limited specific adjustment of isomer ratios in the product. The cleaved product contains amounts of 2,4- and 2,2-methylene-bis-phenyl isocyanates which are disadvantageous for important areas of application.

Not only are the processes described for the preparation of urethanes, which can be thermally cleaved to form polyisocyanates, subject to many drawbacks, but the cleaving processes disclosed in the prior art also have limitations. The thermal cleaving of the polyisocyanates is done either in the gas phase or in the liquid phase. Various undesirable secondary reactions simultaneously take place during the thermal cleaving. These include, for instance, the decarboxylation reaction of the urethanes which may be accompanied by the formation of primary and secondary amines as well as olefins, reactions between the resultant isocyanate and urethane to allophanates and/or amine to ureas, and polymerization of the isocyanates to isocyanurates.

In German Published Application No. 1,944,719 (British Pat. No. 1,247,451), the cleaving of urethanes in the vapor phase is carried out at temperatures from 400° C. to 600° C. in the presence of a Lewis acid catalyst with the isocyanate and the alcohols being separated by fractional condensation. The vapor phase in this case is defined in such a manner that the product mixture, possibly also including the solvent, is present in the vapor phase after the cleaving regardless of whether the urethanes to be cleaved are added in the gaseous, liquid, or solid form. Toluene diisocyanate, for instance, is obtained by means of the pyrolysis of toluene-2,4-diethylurethane in the presence of iron-(III)-chloride.

Drawbacks of the reaction include lower yields combined with considerable quantities of a polymeric byproduct, decomposition of the catalyst and corrosion of the reaction vessel. German Published Application No. 2,410,505 (U.S. Pat. No. 3,870,739) describes a process by which the urethane is cleaved without catalysts at a temperature of 350° C. to 550° C. and pressures of less than the (m+1) times the vapor pressure of the isocyanate product in a catalyst-free pyrolysis zone within 15 seconds. Among others, a drawback of this process is that a large amount of heat required for the endothermic cleaving must be transported to the powdery urethane within a very short period of time. Moreover, a solid polymer, which is produced as byproduct, and its separation make the implementation of a continuous process difficult.

The thermal cleaving of urethanes in the liquid phase is described, for instance, in German Application No. 2,421,503 (U.S. Pat. No. 3,962,302) and German Application No. 2,530,001 (U.S. Pat. No. 3,919,280). According to German Application No. 2,421,503, the urethanes are dissolved in an inert solvent such as alkylbenzene, linear and cyclic hydrocarbons, and/or phthalates, and are cleaved under normal or excess pressures at temperatures of 175° C. to 350° C. The resultant isocyanate and alcohol are isolated and separated with the aid of the solvent as carrier and/or by using an inert gas as carrier. According to German Application No. 2,530,001, higher molecular, possibly substituted, aliphatic, cycloaliphatic, or aromatic hydrocarbons, ethers, esters, or ketones are used as the reaction medium. Only distillation is mentioned for separating the cleaving product with isocyanate, alcohol and carrier materials being distilled overhead whereas the reaction medium remains as bottom fraction.

According to German Published Application No. 2,635,490, urethanes for the manufacture of aromatic isocyanates are brought into contact with a solution of at least one metal ion such as ions of copper, zinc, aluminum, tin, titanium, vanadium, iron, cobalt, and nickel as catalysts. The catalyst is dissolved in a solvent having a boiling point of 200° C. in a metal concentration of at least 0.001 percent by weight relative to the solvent, at temperatures of 150° C. to 350° C. under reduced pressure. The resultant cleaved products are separated by fractional condensation. In accordance with the above-referenced methods, urethanes, dependent upon their structure, can be transformed into isocyanates with yields which are very good in some cases. The manufacture of crude MDI is not described by example in these patents. Differing from the isocyanates which are listed as examples, crude MDI is not completely distillable with the aid of solvents as carriers. Therefore, it can not be isolated as described from catalysts, solvents, unreacted raw materials, and byproducts.

SUMMARY OF THE INVENTION

Applicants have discovered a process for the preparation of aromatic di- and/or polyisocyanates comprising the steps of A. preparing an aromatic di- and/or polyurethane by
1. reacting a primary aromatic di- and/or polyamine with an O-alkyl carbamate at temperatures greater than 100° C.;
2. separating ammonia and other by-products from the aromatic di- and/or polyurethane;

B. cleaving the aromatic di- and/or polyurethane at temperatures of from 175° C. to 600° C.; and C. separating the aromatic di- and/or polyisocyanate resulting from step B.

The process according to this invention can generally be illustrated schematically by equations (I) and (III) or (II) and (III):

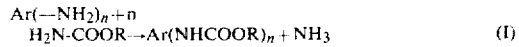

According to a preferred version, the reaction is carried out in the presence of urea and alcohol as represented by the following equation (II):

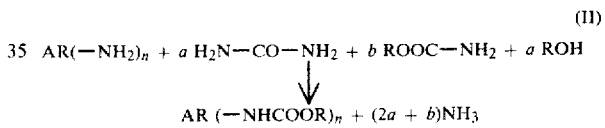

The thermal cleaving of the urethanes takes place in accordance with equation (III).

Reaction (IV) and (V) are specifically related to the preparation of diphenylmethane-diisocyanates and crude MDI.

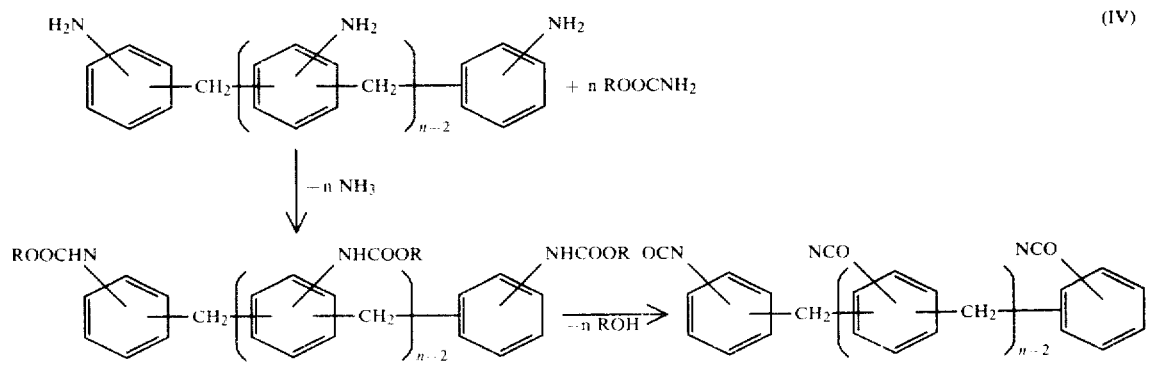

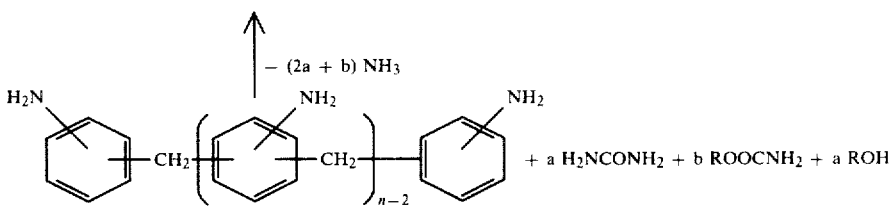

In the equations n, a, and b represent whole numbers with n representing 2 to 8 or higher, preferably 2 to 6, and in which, according to equations (II) and (V), $a + b = n$ and $a:n = 1.5$ to 0.

The formation of aromatic di- and/or -polyurethanes, particularly in one process stage and in good yields, is surprising. At temperatures above 100° C., high molecular, spinnable condensation products are known to result from diamines and urea. See German Pat. No. 896,412. High molecular polyureas, for instance having molecular weights of 8000 to 10,000 and greater, are also obtained if diurethanes are condensed with diamines at temperatures of approximately 150° C. to 300° C. See U.S. Pat. Nos. 2,181,663 and 2,568,885. Mono- and polyurethanes are further cleaved thermally into isocyanates, alcohols and possibly olefins, carbon dioxide, urea and carbodiimide, with the resulting cleaved products again being able to form numerous derivatives such as biurets, allophanates, isocyanurates, polycarbodiimides, and others. See *Journal American Chemical Society*, Vol. 80, page 5495 (1958) and *Journal American Chemical Society*, Vol. 78, page 1946 (1956). Because of these known reactions, it could not be anticipated that the process according to this invention would provide aromatic di- and/or polyurethanes in very good yields under similar reaction conditions.

It is particularly surprising that aromatic di- and/or polyurethanes are obtained in good yields from aromatic primary amines and O-alkylcarbamates according to this invention without adding alcohol, without excess O-alkylcarbamate resulting in considerable decompositions and polycondensations, and without using catalyst to increase the reaction rate and promote the desired product formation. Another surprising fact is that the reaction with urea and alcohol, in the presence of certain catalysts, becomes technically more effective even at low temperatures if it is carried out in combination with larger quantities of O-alkylcarbamate.

In accordance with the process of this invention, aromatic di- and/or polyisocyanates with a high degree of purity can be produced advantageously with large yields. The advantages of the process become particularly apparent when preparing crude MDI which, for the first time, can be produced without using phosgene, carbon monoxide, and toxic and/or expensive catalysts. Moreover, a desirable isomer distribution in the crude MDI can be obtained by controlling the condensation of aniline with formaldehyde and by transforming the resultant mixture of diaminodiphenyl methanes and polyphenyl polymethylene polyamines (crude MDA) into crude MDI.

The aromatic di- and/or polyisocyanates obtained in accordance with this invention are preferably used for the manufacture of polyurethane plastics.

DESCRIPTION OF THE PREFERRED EMBODIMENT

In order to prepare the aromatic di- and/or polyisocyanates of this invention, an aromatic di- and/or polyurethane is first prepared. The aromatic polyurethane is then thermally cleaved into the corresponding aromatic di- and/or polyisocyanate.

The aromatic di- and/or polyurethane is prepared by the reaction of primary aromatic di- and/or polyamines and O-alkyl carbamates. Preferably the reaction of the di- and/or polyamines is carried out in the presence of an alcohol and urea. The reaction may also be carried out in the presence of catalysts.

Aromatic di- and/or polyamines which can be employed in accordance with this invention are unsubstituted and substituted primary aromatic di- and/or polyamines. Representative amines include the following: aromatic diamines such as 1,3- and 1,4-diaminobenzene; a 1,3-diaminobenzene substituted in the 2 and/or 4 position by a nitro, methyl, ethyl, n-propyl, isopropyl, n-butyl, isobutyl, secondary butyl, tertiary butyl, methoxy, ethoxy, n-propoxy, isopropoxy, n-butoxy, isobutoxy, secondary butoxy, tertiary butoxy group or a halogen atom, preferably a fluorine or chlorine atom; or a 1,4-diaminobenzene, 1,5- and 1,8-diaminonaphthylene, 4,4'-diaminodiphenyl, 2,2'-, 2,4'- and 4,4'-diaminodiphenylmethane and the corresponding isomer mixtures; and aromatic polyamines such as 1,3,5-triaminobenzene, 2,4,6-triaminotoluene, 1,3,5-triaminonaphthalene; and polyphenyl polymethylene polyamines, as well as mixtures of diaminodiphenyl methanes and polyphenyl polymethylene polyamines substituted in the 2 position and which are produced according to known methods by condensation of aniline and formaldehyde in the presence of preferably mineral acids as catalysts.

The following substances were proven to work particularly well and are, therefore, used on a preferred basis. These are 2,4- and 2,6-diaminotoluene and the corresponding isomer mixtures, 1,5-diaminonaphthalene, 3,3'-ditoluene-4,4-diamine, 2,2'-, 2,4'- and 4,4'-diaminodiphenylmethane and the corresponding isomer mixtures, and mixtures of diaminodiphenylmethane isomers and polyphenyl polymethylene polyamines.

During the reaction, the amino groups are transformed into alkoxycarbonylamino groups regardless of whether or not the remaining substituents are retained unchanged or are also changed.

O-alkylcarbamates, which are suitable for the reaction with the primary aromatic di- and/or polyamines, have the formula $H_2N—COOR$ in which R represents a substituted or unsubstituted aliphatic, cycloaliphatic, or aromatic radical. Representative examples include O-alkylcarbamates based on primary aliphatic monoalcohols having 1 to 20 carbon atoms, preferably 1 to 10 carbon atoms, such as methyl carbamate, ethyl carbamate, propyl carbamate, n-butyl carbamate, isobutyl carbamate, 2- and 3-methylbutyl carbamate, neopentyl carbamate, pentyl carbamate, 2-methylpentyl carbamate, n-hexyl carbamate, 2-ethylhexyl carbamate, heptyl carbamate, n-octyl carbamate, n-nonyl carbamate, n-decyl carbamate, and n-dodecyl carbamate, 2-phenylpropyl carbamate, and benzyl carbamate; and O-alkyl carbamates based on secondary aliphatic and cycloaliphatic monoalcohols having 3 to 15 carbon atoms, preferably 3 to 6 carbon atoms such as isopropyl carbamate, secondary butyl carbamate, secondary isoamyl carbamate, cyclopentyl carbamate, cyclohexyl carbamate, tertiary butylcyclohexyl carbamate, and bicyclo(2,2,1)-heptyl carbamate. Preferably used are methyl carbamate, ethyl carbamate, propyl carbamate, butyl carbamate, isobutyl carbamate, 2- and 3-methylbutyl carbamate, pentyl carbamate, hexyl carbamate, 2-ethylhexyl carbamate, heptyl carbamate, octyl carbamate, and cyclohexyl carbamate.

As was previously mentioned, the reaction of the aromatic di- and/or polyamines is preferably carried out in the presence of alcohols and urea. Urea is appropriately used in its commercially available form and purity.

Any desired substituted or unsubstituted primary or secondary aliphatic alcohol, as well as mixtures thereof, may be used as alcohols. Preferably used is the alcohol corresponding with the O-alkylcarbamates. Representative examples include primary aliphatic alcohols having 1 to 20 carbon atoms, preferably 1 to 10 carbon atoms such as methanol, ethanol, propanol, n-butanol, 2-methylbutanol, n-pentanol, neopentyl alcohol, 2-methylpentanol, n-hexanol, n-heptanol, n-octanol, nonanyl, n-decanol, and n-dodecanol, secondary aliphatic and cycloaliphatic alcohols having 3 to 15 carbon atoms, preferably 3 to 16 carbon atoms such as isopropanol, secondary butanol, secondary isoamyl alcohol, cyclopentanol, 2,3- or 4-methylcyclohexanol, cyclohexanol and bicyclo-(2,2,1)-heptanol. Preferably used monoalcohols are methanol, ethanol, propanol, n-butanol, isobutanol, 2-ethylbutanol, 2- and 3-methyl-n-butanol, n-pentanol, n-hexanol, 2-ethylhexanol, heptanol, octanol, and cyclohexanol. If so desired, the alcohols may be mixed with other organic solvents which are inert under the reaction conditions.

The primary aromatic di- and/or polyamines are reacted with the O-alkylcarbamates and alcohols in such quantities that the ratio of amino groups of the primary aromtic amines to O-alkylcarbamates to hydroxyl groups of the alcohol is 1 to 0.5:20 to 0:100, preferably 1 to 1:10 to 1:30, and particularly 1 to 1:6 to 2:20. If urea is also used, the ratio of amino groups of the primary aromatic amines to the total amino groups of O-alkylcarbamate and urea is 1 to 0.5:20, preferably 1 to 1:10, and particularly 1 to 1:6, and the mole ratio of urea to amino groups of the primary aromatic amines being equal to or less than 1.5, preferably 1.25 to 0.75, and the mole ratio of urea to alcohol being equal to or less than 1.

It is not necessary to separately produce the O-alkylcarbamates. According to an easily implemented, preferably used version, pre-produced O-alkylcarbamate is used together with urea and alcohol, and after extensive to complete reaction of the primary aromatic di- and/or polyamine, the O-alkylcarbamate is separated by means of distillation and is recycled if so required. The aromatic di- and/or polyurethane, according to the reaction step of this invention, may also be produced on a continuous basis.

In order to increase the rate of reaction and improve the yield, the aromatic di- and/or polyurethanes are preferably prepared in the presence of at least one catalyst. Suitable catalysts are inorganic or organic compounds containing one or more, preferably one, cation of metals of groups IA, IB, IIA, IIB, IIIA, IIIB, IVA, IVB, VA, VB, VIB, VIIB and VIIIB of the periodic system defined according to the *Handbook of Chemistry and Physics*, (14th edition, published by Chemical Rubber Publishing Company, 2310 Superior Avenue, N.E., Cleveland, Ohio). The compounds include, for instance, halides, such as chlorides and bromides, sulfates, phosphates, nitrates, borates, alcoholates, phenylates, sulfonates, oxides, oxide hydrates, hydroxides, carboxylates, chelates, carbonates and thio or dithiocarbamates. The compounds may include cations of the following metals: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron, cobalt and nickel. Preferably used are the cations of lithium, calcium, aluminum, tin, bismuth, antimony, copper, zinc, titanium, vanadium, chromium, molybdenum, manganese, iron and cobalt. Without recognizable marked drawbacks, these catalysts can also be used in the form of their hydrates or ammoniates.

Representative examples of typical catalysts include the following compounds: lithium methanolate, lithium ethanolate, lithium propanolate, lithium butanolate, sodium methanolate, potassium-tertiary butanolate, magnesium methanolate, calcium methanolate, tin-(II)-chloride, tin-(IV)-chloride, lead acetate, lead phosphate, antimony-(III)-chloride, antimony-(V)-chloride, aluminum isobutylate, aluminum trichloride, bismuth-(III)-chloride, copper-(II)-acetate, copper-(II)-sulfate, copper-(II)-nitrate, bis(triphenylphosphineoxido)copper-(2)-chloride, copper molybdate, silver acetate, gold acetate, zinc oxide, zinc chloride, zinc acetate, zinc acetonylacetate, zinc octoate, zinc oxylate, zinc hexylate, zinc benzoate, zinc undecylinate, cerium-(IV)-oxide, urinylacetate, titanium tetrabutynolate, titanium tetrachloride, titanium tetraphenylate, titanium naphthanate, vanadium-(III)-chloride, vanadium-acetonylacetonate, chromium-(III)-chloride, molybdenum-(VI)-oxide, molybdenum acetonylacetonate, tungston-(VI)-oxide, manganese-(II)-chloride, manganese-(II)-acetate, manganese-(III)-acetate, iron-(II)-acetate, iron-(III)-acetate, iron phosphate, iron oxylate, iron-(III)-chloride, iron-(III)-bromide, cobalt acetate, cobalt chloride, cobalt sulfate, cobalt naphthenate, nickel chloride, nickel acetate and nickel naphthenate, as well as their mixtures.

The catalysts are advantageously used in quantities corresponding with 0.0001 to 0.1, preferably 0.0005 to 0.05, equivalents of the metal cations relative to the amino groups of the aromatic di- and/or polyamines. The metal ions can also be used bonded to ion exchangers in the heterogeneous phase.

The reaction takes place at increased temperatures, for instance, at temperatures from 100° C. to 250° C., preferably 130° C. to 210° C., and particularly 150° C. to 190° C., and under pressures of 0.1 bar to 120 bars, preferably 0.5 bar to 60 bars, particularly 1 bar to 40 bars. It has proven to be particularly advantageous to separate the resultant ammonia from the reaction mixture, for instance, by means of distillation. At a given temperatures, the reaction is then preferably implemented at a pressure under which the resultant ammonia can be distilled selectively from the reaction mixture. The corresponding values may be taken from tables with the physical data for ammonia and alcohols. The reaction times for the referenced temperature ranges are 0.5 to 100 hours, preferably 1 to 50 hours, and particularly 2 to 25 hours.

An advantageous process for preparing the aromatic di- and/or polyurethanes of this invention will now be described. The primary aromatic di- and/or polyamines, O-alkylcarbamates, and possibly alcohols, urea and catalysts are mixed in the referenced quantity ratios. The ingredients are heated in a reaction vessel equipped with a device for separating the ammonia in the presence or absence of stirring. After the reaction has been completed, the resultant ammonnia can be separated. Preferably, however, it is removed by distillation on a continuous or batch type basis during the reaction process. It may be advantageous, particularly when the reaction takes place in the presence of low molecular alcohols under pressure, to separate the ammonia with the aid of a stripping agent which is inert under the reaction conditions, such as a gas such as nitrogen. Before or after separating the catalyst and removing solids by filtration, the aromatic di- and/or polyurethane is subsequently isolated from the resultant reaction mixture. This can be done by distillation of the excess O-alkylcarbamate and/or the alcohol, by partial distillation of the excess O-alkylcarbamate and/or the alcohol and crystallizing, by crystallizing, or precipitating with or also by transcrystallization from other solvents. If required, the catalysts can be separated, for instance, by means of sedimentation, filtration, washing, or bonding with ion exchangers.

The aromatic di- and/or polyurethanes are thermally cleaved to prepare aromatic di- and/or polyisocyanates. They may be thermally cleaved in the gas phase or the liquid phase. In the gas phase, the aromatic di- and/or polyurethanes are cleaved according to basically known processes at temperatures of 300° C. to 600° C. The cleaving process may take place in the absence of catalysts in accordance with the process described in German Published Application No. 2,410,505 (U.S. Pat. No. 3,870,739), or in the presence of catalysts, for instance, in accordance with the process described in German Published Application No. 1,944,719 (British Pat. No. 1,247,451). In the liquid phase, the di- and/or polyurethanes can be cleaved at temperatures of 175° C. to 350° C. in the presence of solvents free of catalysts, for instance, according to the process described in German Application No. 2,421,503 (U.S. Pat. No. 3,962,302) or German Application No. 2,530,001 (U.S. Pat. No. 3,919,280), or in the presence of solvents and catalysts, for instance, according to the process described in German Published Application No. 2,635,490.

Since the removal of dissolved catalysts from the reaction products is a problem, the uncatalyzed thermal cleaving of the aromatic di- and/or polyurethanes is recommended, particularly for nondistillable polyisocyanates. If catalysts are used, it has been found to be advantageous to accelerate the thermal cleaving process by heterogeneous catalysis with metals selected from the group consisting of zinc, aluminum, titanium, iron, chromium, cobalt, and nickel. These metals may be used in combination with other metals such as vanadium and tungsten. The catalyst preferably should have a large surface area, for instance, in the form of metal powders or granules, having average diameters of 1 to 10 millimeters, shavings, or wool. The metals are not only good thermal conductors, but in addition to this, they have a technically good catalytic effect. Consequently, the reaction temperatures and/or reaction times are reduced, and secondary reactions, such as polymerizatons are less pronounced.

Zinc and aluminum are preferred because of their excellent activity. In cleaving aryl diurethanes in the gas phase in the presence of zinc and aluminum in a heterogeneous phase, for instance, one can reduce the cleaving temperature by 50° C. to 100° C., and achieve the same cleaving rate when compared with other known processes.

The catalysts may be used in various arrangements. They can be used as fixed beds, for instance, by charging variously shaped reactors, such as tube, tank or boiler type reactors, with metal granules, rings, shavings, or wool, so that the reaction mixture can be continuously directed through the fixed catalyst bed. Alternatively, the catalyst may be suspended in a mixing reactor.

If solvents are used, they should be inert under the reaction conditions with respect to the isocyanates and the other components and have a different boiling point. Solvents with boiling points between those of the aromatic di- and/or polyisocyanates and the separated alcohol are advantageous for cleaving in the liquid phase when the di- and/or polyisocyanate is isolated as nondistillable bottom fraction. However, solvents can also be used as diluting agent for cleaving in the gas phase and can possibly facilitate the isolation of the isocyanate by fractional condensation without resulting in the recombination of the isocyanate with the alcohol. Solvents with boiling points higher than the boiling points of the cleaved products are preferred for cleaving di- and/or polyurethanes in the liquid phase into di- and/or polyisocyanates which are isolated by distillation. A solvent boiling between the alcohol and isocyanate may possibly be employed in order to improve the isolation of alcohol and isocyanate.

Proven to work particularly well as a solvent and, therefore, used on a preferable basis is dibenzylnaphthalene. This is prepared by benzylation of naphthalene and benzyl chloride. It can be used for cleaving di- and/or polyurethanes in the liquid phase into aromatic di- and/or polyisocyanates, where the boiling point of the polyisocyanates is lower than the boiling point of dibenzylnaphthalene.

It is advantageous if the aromatic di- and/or polyurethanes are soluble in the solvent, although this is not absolutely essential. The solvent acts as the heating medium which serves to introduce heat to the reaction system and allows the reaction temperature to be uniformly distributed.

Other solvents which can be used include aliphatic hydrocarbons such as the higher alkanes such as decane, undecane, dodecane, tridecane, tetradecane, pentadecane, hexadecane, heptadecane, decaline, liquid paraffin, crude oil fractions of paraffins which are normally used as lubricating oils, cooling oils, or cutting oils; alicyclic hydrocarbons such as fractions of the naphthene series; unsubsituted and substituted aromatic hydrocarbons such as naphthalene, 1- and 2-methylnaphthalene, 1,2-, 1,4-, 1,6-, 2,7-, 2,6- and 2,3-dimethylnaphthalene, 1-ethylnaphthalene, phenylnaphthalene, benzylnaphthalene, toluene, 1,2-, 1,3- and 1,4-dimethylbenzene, 1,2,4- and 1,3,5-trimthylbenzene, 1,2,3,5- and 1,2,4,5-tetramethylbenzene, 1,3,5-triethylbenzene, hexyl, 4,4'-dimethyldiphenyl, dibenzyl, diphenylmethane, and 4,4'-dimethyldiphenylmethane; halogen-substituted aromatic hydrocarbons such as chlorobenzene, 1,2- and 1,4-dichlorobenzene, 1,4-diiotobenzene, 1,2,3- and 1,3,5-trichlorobenzene, 1,2,3,4-, 1,2,3,5- and 1,2,4,5-tetrachlorobenzene, pentachlorobenzene, 1- and 2-fluoronaphthalene, 1- and 2-chloronaphthalene, 1- and 2-iotonaphthalene, and diphenyldichloromethane; nitro-group containing aromatic hydrocarbons such as nitrobenzene, 3-nitrotoluene, 2-nitro-m-xylene, 5-nitro-m-xylene, and 4-nitroanisol, aliphatic and aromatic ketones such as cyclohexanone, cycloheptanone, di-n-butylketone, di-n-amylketone, alphatetralon, acetophenon, propiophenon, benzophenon, 3-methylbenzophenon, dodecanon-2 and tridecanon-2; sulfone; and carboxylic esters such as sulfolan, diethylsulfone, dimethylester of phthalic acid, diethylester of phthalic acid, propylester of benzoic acid, and ethylester of lauric acid, and ethers such as diethylene glycol dimethyl ether, diethylene glycol diethyl ether, diisoamyl ether, di-n-amyl ether, resorcindimethyl ether, resorcindiethyl ether, phenyloctylether, phenylbenzyl ether, dibenzylether, diphenyl ether, α-methylnapthyl ether and β-ethylnaphthyl ether.

The di- and/or polyurethanes may be thermally cleaved in the gas phase or in the liquid phase by a batch type method or on a continuous basis under reduced, normal or increased pressure. The cleaving and separating of the products by distillation of the alcohol, possibly the di- and/or polyisocyanate, and/or the solvent, can take place simultaneously or in sequence. As a rule, the cleaving process in the gas phase takes place under reduced pressure, the maximum of which is equal to the boiling point of the reaction mixture at a given temperature. With simultaneous cleaving and separation in the liquid phase, a temperature-pressure ratio is advantageously chosen which corresponds to the boiling point of the low boiling component of the bottom fraction. In a closed system, for instance in a tube separating reactor, the cleaving advantageously takes place without increase in the system pressure.

The raw materials may be introduced into the reactor either in the gaseous, molten, or solid form, for instance as a powder, as a suspension, or as a solution in an inert solvent. The reactor is selectively kept at a certain temperature and a certain pressure. An aromatic diurethane, for instance, in the vapor, liquid, or solid phase, corresponding with 0.1 urethane equivalent to 20 urethane equivalents, preferably 1 urethane equivalent to 10 urethane equivalents per liter an hour, is introduced into a tube reactor charged with zinc shavings at a temperature from 300° C. to 400° C., preferably 330° C. to 380° C., and at pressure of 1 millibar to 1 bar, preferably of 1 millibar to 100 millibars. The aromatic diisocyanate, the alcohol, and possibly non-reacted aromatic diurethane is advantageously fractionally condensed via a column while adding an inert solvent, the boiling point of which is located between the boiling points of alcohol and isocyanate. The solution of a di- and/or polyurethane in an inert solvent can be led through a tube reactor charged with zinc or aluminum granules at a temperature of 175° C. to 350° C., preferably 220° C. to 320° C., and the product can subsequently be directed into a column or through a cascade of several cleaving reactors and separating columns in alternate arrangement in order to facilitate the separation.

According to another preferred version, the solution is continuously introduced into a reactor while the alcohol is simultaneously being separated, possibly with the aid of a stripping agent, or an intermediate boiler. The di- and/or polyisocyanate is removed via one or more separating columns and the solvent, which is removed as a bottom fraction is recycled.

In another preferred process variation, the aromatic di- and/or polyurethanes, for instance, crude MDU, can be cleaved in a suitable solvent as described above in the liquid phase. Simultaneously, the alcohol may be distilled with the solvent being refluxed. The solvent may then be carefully distilled, possibly by stripping, with a short residence time. The aromatic di- and/or polyisocyanate is refluxed and discharged as a bottom fraction. In this case, it has proven to be advantageous to remove part of the aromatic di- and/or polyisocyanate with the solvent by distillation and to recycle the mixture into the cleaving reactor.

The parts referred to in the examples which follow are parts by weight.

EXAMPLE 1

In a reaction vessel, 61 parts of 2,4-diaminotoluene, 250 parts of ethyl carbamate, 5 parts of iron-(II)-acetate, and 140 parts of ethanol are heated to 180° C. to 190° C. for 14 hours with a pressure of 8 bars to 10 bars being maintained in the reaction vessel via a pressure regulation valve. Using 30 liters of nitrogen per liter of reaction mixture an hour as the stripping agent, the ammonia formed during the reaction is continuously removed by means of distillation. After the reaction has been completed, the reaction solution is analyzed gas chromatographically, using the internal standard method, as well as by means of high pressure liquid chromatography, using the external standard method. It is found that 94 percent of the 2,4-diaminotoluene was reacted resulting in 113 parts of 2,4-bis-(ethoxycarbonylamino)toluene (90.4 percent theory relative to the reacted 2,4-diaminotoluene). In addition to this, the reaction solution contains a mixture of 2-amino-4-(ethoxycarbonylamino)toluene and 4-amino-2-(ethoxycarbonylamino)toluene.

Excess ethanol and excess ethyl carbamate are distilled from the reaction solution. The residue is dissolved in 1000 parts of methylene chloride, and is washed several times with water. At this point, the methylene chloride is removed, 200 parts of ethanol are added, and the product is placed into an ice-sodium chloride mixture. After some time, 85 parts of 2,4-bis(ethoxycarbonylamino)toluene (68 percent of theory relative to reacted 2,4-diaminotoluene) having a melting point of 107° C. to 109° C., will crystallize. Via a powder metering device, the diurethane obtained in this manner is introduced continuously at a rate of approximately 200 liters per liter of reaction space an hour into a tube reactor of quartz glass filled with zinc shavings and heated to 360° C. A pressure of 15 millibars to 25 millibars is maintained in the heated reactor. The escaping product gases are fractionally condensed. It is found that 49.5 parts of toluene diisocyanate (TDI) [89.0 percent of theory relative to the cleaved 2,4-bis(ethoxycarbonylamino)toluene] have been obtained in a water-cooled receiving vessel. By means of gas chromatography, it is shown that a mixture of 4-(ethoxycarbonylamino)toluene-2-isocyanate and 2-(ethoxycarbonylamino)toluene-4-isocyanate is in the vessel.

EXAMPLE 2

In a reaction vessel, 61 parts of 2,4-diaminotoluene, 450 parts of methyl carbamate, 5 parts of zinc acetate, 60 parts of urea, and 192 parts of methanol are heated to 180° to 190° C. for 16 hours with a pressure of 11 to 13 bars being maintained in the reaction vessel via a pressure regulation valve. Using 25 liters of nitrogen per liter of reaction mixture an hour as a stripping agent, the ammonia formed during the reaction is continuously removed by means of distillation. After the reaction has been completed, the reaction solution is analyzed gas chromatographically using the internal standard method as well as by means of high pressure liquid chromatography using the external standard method. It is found that 98 percent of the 2,4-diaminotoluene was reacted resulting in 97 parts of 2,4-bis(methoxycarbonylamino)toluene (83.2 percent of theory relative to the reacted 2,4-diaminotoluene). The reaction solution also contains a mixture of 2-amino-4-(methoxycarbonylamino)toluene and 4-amino-2-(methoxycarbonylamino)toluene. Excess methanol and excess methyl carbamate are distilled from the chloride mixture. After some time, 86 parts of 2,4-bis(methoxycarbonylamino)toluene will crystallize having a melting point of 158° C. to 162° C.

Via a powder metering device, the resultant diurethane is continuously fed at a rate of approximately 250 liters per liter of reaction space an hour into a quartz glass tube reactor filled with zinc shavings and heated to 350° C. A pressure of 10 millibars to 15 millibars is maintained in the reactor. The escaping product gases are fractionally condensed. It is found that 60 parts of toluene diisocyanate (TDI) [95.4 percent of theory relative to reacted 2,4-bis(methoxycarbonylamino)toluene] have been obtained in a water-cooled receiving vessel.

EXAMPLE 3

In a reaction vessel, 40 parts of 2,4-diaminotoluene, 240 parts of hexyl carbamate, 1.5 parts of cobalt acetate, and 170 parts of hexanol are heated to 155° C. to 175° C. for a period of 15 hours with the resultant ammonia being removed by continuous distillation. After the reaction is completed, the reaction solution is examined by high pressure liquid chromatography according to the external standard method. It is found that the 2,4-diaminotoluene has been completely reacted resulting in 119 parts of 2,4-bis(hexoxycarbonylamino)toluene (96 percent of theory relative to the reacted 2,4-diaminotoluene).

The catalyst used is then removed. After washing the filtrate with water, excess hexanol and excess hexyl carbamate are removed by distillation under reduced pressure. The resultant 134 parts of a distillation residue are dissolved in 300 parts of dibenzylnaphthalene. With a feed rate of 350 liters per liter of reaction space an hour, this solution is fed into a quartz glass tube reactor filled with aluminum granules and heated to a temperature of 320° C. Using 35 liters of nitrogen per liter of reaction mixture an hour, the hexanol formed during the reaction is separated in its gaseous form and is condensed in several water-cooled receiving vessels which are connected in sequence. The result is 358 parts of reaction discharge from which 53 parts of toluene diisocyanate (92.9 percent of theory relative to the reacted 2,4-diaminotoluene) are obtained by means of vacuum distillation at 76° C. to 82° C. and 0.2 millibars.

EXAMPLE 4

In a reaction vessel, 100 parts of a commercially available crude MDA mixture, 56 percent of which consists of diaminodiphenylmethane and 44 percent of which consists of polyphenyl polymethylene polyamines, 30.3 parts of urea, 300 parts of hexyl carbamate, 1.5 parts of cobalt acetate, and 260 parts of hexanol are heated to 155° C. to 175° C. for 25 hours with the resultant ammonia being continuously removed by means of distillation. After the reaction has been completed, the reaction solution is examined by high pressure liquid chromatography. This examination shows that a mixture of bis(hexoxycarbonylamino)diphenylmethanes and poly(hexoxycarbonylamino)-polyphenyl polymethanes has been formed which is identical to a comparison product produced from "crude MDI" and hexanol.

The catalyst is allowed to settle. The solution is filtered followed by a washing with water. Excess hexanol and excess hexylcarbamate are removed by distillation under a vacuum. Obtained are 233 parts of distillation residue which are dissolved in 750 parts of decylbenzene. With a feed rate of 300 liters per liter of reaction space an hour, this solution is fed into a quartz glass tube reactor filled with zinc shavings and heated to 300° C. The hexanol formed from the cleaving process is separated in its gaseous form and is condensed in several water-cooled receiving vessels. At a pressure of 1 millibar to 2 millibars, the cleaving solvent is continuously distilled from the reaction discharge in such a manner that the bottom fraction is essentially solvent free. The distillate contains approximately 0.4 percent of diphenylmethane diisocyanate.

Obtained are 113 parts of distillation residue consisting of a mixture of 51 percent diphenylmethane diisocyanate and 49 percent polyphenyl polymethylene polyisocyanate (crude MDI).

EXAMPLE 5

In a reaction vessel, 50 parts of 4,4'-diaminodiphenylmethane, 360 parts of hexyl carbamate, 1 part of cobalt acetate, and 260 parts of hexanol are heated to 155° C. to 175° C. for 35 hours. After cooling, the solution is filtered from the settled catalyst and the reaction mixture is analyzed by means of high pressure liquid chromatography using the external standard method. It is found that the 4,4'-diaminodiphenylmethane has been completely reacted. After washing the reaction discharge with water, excess hexanol and excess hexyl carbamate are removed by distillation. The resultant 121 parts of distillation residue are dissolved in 120 parts of 1,2,4,5-tetramethylbenzene. With a feed rate of 100 liters per liter of reaction space an hour, this solution is fed into a quartz glass tube reactor filled with aluminum shavings in which a pressure of 5 millibars to 10 millibars is maintained, and heated to a temperature of 350° C. The hexanol formed by the cleaving process is separated in its gaseous form and is condensed with evaporated tetramethylbenzene in a water-cooled receiving vessel. The reaction discharge consists of 93 parts of a solution of 51 parts of 4,4'-diphenylmethane diisocyanate (80.8 percent of theory relative to the reacted 4,4'-diaminodiphenylmethane) in tetramethylbenzene.

EXAMPLE 6

In a reaction vessel, 15.8 parts of 1,5-diaminonaphthalene, 89 parts of ethyl carbamate, 12 parts of urea, 0.15 part of cobalt acetate, and 46 parts of ethanol are heated to 180° C. for a period of 12 hours with the pressure being maintained at 8 bars to 10 bars via a pressure regulation valve. Using 20 liters of nitrogen per liter of reaction mixture an hour as stripping agent, the ammonia formed during the reaction is continuously removed by means of distillation. After the reaction has been completed, excess ethanol, excess ethyl carbamate, and unreacted 1,5-diaminonaphthalene are removed by distillation which in part takes place under vacuum. After adding 450 parts of ethanol, the solution is placed in an ice-sodium chloride solution whereupon 25 parts of 1,5-bis(ethoxycarbonylamino)naphthalene (82.8 percent of theory relative to the reacted 1,5-diaminonaphthalene) will crystallize after some time. This product has a melting point of 217° C. to 223° C. The 1,5-bis(ethoxycarbonylamino)naphthalene is fed into a tube reactor filled with zinc shavings via a powder metering device at a rate of 450 liters per liter of reaction space an hour and is heated to 350° C. A pressure of 1 millibar to 3 millibars is maintained in the cleaving reactor. The escaping product gases are fractionally condensed. Obtained in a first water-cooled receiving vessel are 14 parts of 1,5-naphthalene diisocyanate (NDI) [80.5 percent of theory relative to the cleaved 1,4-bis(ethoxycarbonylamino)naphthalene] having a melting point of 129° C. to 132° C.

The embodiments of the invention in which an exclusive privilege or property is claimed are defined as follows:

1. A process for the preparation of an aromatic di- and/or polyisocyanate comprising the steps of
A. preparing an aromatic di- and/or polyurethane by
 1. reacting a primary aromatic di- and/or polyamine with an O-alkyl carbamate at temperatures greater than 100° C.;
 2. separating ammonia and other by-products from the aromatic di- and/or polyurethane;
B. cleaving the aromatic di- and/or polyurethanes at temperatures from 175° C. to 600° C.; and
C. isolating the di- and/or aromatic polyisocyanate resulting from step B.

2. The process of claim 1 wherein step A (1) is carried out in the presence of urea and an alcohol.

3. The process of claim 1 wherein step A (1) is carried out in the presence of a catalyst compound containing one or more cations of metals selected from groups IA, IB, IIA, IIB, IIIA, IIIB, IVA, IVB, VA, VB, VIA, VIB, VIIB, VIIIB of the periodic chart.

4. The process of claim 2 wherein the ingredients used to prepare the aromatic di- and/or polyurethanes are reacted in such quantities that the ratio of amino groups of the aromatic di- and/or polyamines to amino groups of O-alkyl carbamate to hydroxyl groups of the alcohol is 1 to 0.5:20 to 0:100.

5. The process of claim 2 wherein the mole ratio of urea to alcohol is equal to or less than 1.

6. The process of claim 1 or 2 carried out in the presence of urea wherein a maximum of 1,5 equivalents of urea, relative to the amino groups of the polyamines, is used.

7. The process of claim 1 wherein the polyamine is selected from the group consisting of 2,4- and 2,6-diaminotoluene and the corresponding isomer mixtures, 1,5-diaminonaphthalene, 3,3'-ditoluene-4,4'-diamine, 2,2'-, 2,4'- and 4,4'-diaminodiphenylmethane and the corresponding isomer mixtures, as well as mixtures of diaminodiphenylmethane isomers and polyphenyl polymethane polyamines.

8. The process of claim 1 wherein the O-alkylcarbamates are produced from carbamic acid and aliphatic and cycloaliphatic monoalcohols having 1 to 10 carbon atoms in the alcohol radical.

9. The process of claim 1 wherein the aromatic polyurethanes are thermally cleaved in the liquid phase in a solvent at temperatures of 175° C. to 350° C. in the presence of metals selected from the group consisting of zinc, aluminum, titanium, iron, chromium, cobalt and nickel as catalysts which are present in the heterogeneous phase.

10. The process of claim 9 wherein said solvent has a boiling point which is located between the resultant polyisocyanate and that of the separated alcohol.

11. The process of claim 9 wherein the cleaving catalyst has a large surface area, said catalyst being aluminum or zinc being present in the heterogeneous phase.

12. The process of claim 1 wherein the aromatic polyurethane is thermally cleaved in the gas phase at temperatures of 300° C. to 600° C. in the presence of zinc or aluminum.

13. The process of claim 12 wherein the zinc or aluminum catalyst has a large surface area.

14. The process of claims 1 or 9 wherein the aromatic polyurethane is thermally cleaved in the liquid phase such that part of the resultant aromatic polyisocyanate is distilled with the solvent, is recycled with the solvent to the cleaving reactor, and the remaining part of the aromatic polyisocyanate is discharged as a bottom fraction.

* * * * *